United States Patent [19]

Kelsey

[11] 4,198,528
[45] Apr. 15, 1980

[54] PREPARATION OF DI-TERTIARY PEROXIDES

[75] Inventor: Donald R. Kelsey, Piscataway, N.J.

[73] Assignee: Union Carbide Corporation, New York, N.Y.

[21] Appl. No.: 872,179

[22] Filed: Jan. 25, 1978

[51] Int. Cl.$^2$ ............................................. C07C 179/06
[52] U.S. Cl. .................................... 568/578; 568/561
[58] Field of Search ............... 260/610 R, 610 A, 610; 568/578, 561

[56] References Cited

U.S. PATENT DOCUMENTS 3,310,588   3/1967   Kloosterman et al. .......... 260/610 R

FOREIGN PATENT DOCUMENTS 792558   3/1958   United Kingdom ................ 260/610 R

*Primary Examiner*—Werren B. Lone
*Attorney, Agent, or Firm*—Bernard Francis Crowe

[57] ABSTRACT

The reaction rates for the interaction of tertiary hydroperoxides with tertiary alcohols to afford di-tertiary peroxides are increased by carrying out the reaction in the presence of a carboxylic acid anhydride.

12 Claims, No Drawings

PREPARATION OF DI-TERTIARY PEROXIDES

BACKGROUND OF THE INVENTION

This invention pertains to the preparation of di-tertiary peroxides and more particularly to the removal of water by chemical reaction in situ.

Di-tertiary alkyl or aryl peroxides have been prepared by the condensation of a hydroperoxide and an alcohol in the presence of an acid catalyst. This reaction is depicted in equation (1) below:

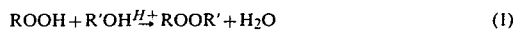

$$ROOH + R'OH \overset{H^+}{\rightleftharpoons} ROOR' + H_2O \qquad (1)$$

It has been demonstrated in such syntheses as the preparation of dicumyl peroxide from cumene hydroperoxide and cumyl alcohol that the removal of the water formed in reaction (1) facilitates the reaction especially by reducing the reaction time needed to reach a given conversion of reactants to products. This permits, for example, increased production capacity from a given reactor. However, all of the prior art methods for removing this water of reaction have called for the use of either physical separation or the formation of physically hydrated species with an anhydrous substance. Thus, for example, sulfuric acid has been used as a dehydrating agent by Y. Tsunoda, Nippon Kagaku Zasshi, 81, 310 (1960), nitrogen gas has been bubbled through the reaction mixture by Y. Tsunoda, Kogyo Kagaku Zasshi, 63, 837 (1960), reduced pressure has been used to remove water as disclosed in U.S. Pat. Nos. 3,337,639 and 3,308,163, and azeotropic agents have been used to remove water as disclosed in Canadian Pat. No. 839,312, U.S. Pat. Nos. 3,584,057, 3,337,369, 3,308,163 and 3,681,316. Dihydrates have been formed using anhydrous oxalic acid, as disclosed in U.S. Pat. No. 3,310,558. Dried silica-alumina was used in Japanese Pat. No. 15,970 (1964) (Chemical Abstracts 62:10376e). Anhydrous magnesium sulfate was used to remove water as a hydrate as disclosed in U.S. Pat. No. 3,833,664.

STATEMENT OF THE INVENTION

An improved method for the preparation of ditertiary peroxides by the interaction of a tertiary aryl or tertiary alkyl hydroperoxide with a tertiary aryl or tertiary alkyl alcohol in the presence of a catalytic amount of a strong acid catalyst has been devised which comprises carrying out said interaction in the presence of an anhydride of carboxylic acids having a $pK_a > 2.85$ in a molar ratio of hydroperoxide:alcohol:anhydride of about 1.0:0.2–2.5:0.2–2.0 at a temperature of about $-10°$ C. to about $120°$ C.

This method provides for the removal of water of reaction by a chemical reaction in situ by the hydrolysis of the anhydride. This results in a high yield of di-tertiary peroxides and reduction in the reaction time needed to obtain a given conversion of reactant hydroperoxide compared to the reaction time required in the absence of the anhydride. This in situ reaction obviates the need for physical separation methods during the reaction or the use of dehydrated desiccating salts which must then be recovered for re-use by treatment under vacuum and/or high temperature or disposed of.

The carboxylic acid anhydrides used in this invention are readily hydrolyzable to weak carboxylic acids having dissociation constants, expressed as $pK_a$, of more than 2.85 when measured in water at 25° C. The term "readily hydrolyzable" refers to the observed hydrolysis rate of the anhydride in water or organic solvent-water solutions at 10°–40° C. relative to the observed hydrolysis rate of acetic anhydride under similar conditions. The ratio of the hydrolysis rates of "readily hydrolyzable" anhydrides used in this invention relative to acetic anhydride is at least about 0.2:1.0. These anhydrides should also be at least partially soluble in the reaction media of this invention including both the tertiary hydroperoxides and tertiary alcohols as well as any solvents which may be used. Carboxylic acid anhydrides meeting the requirements of this invention include those represented by the formula:

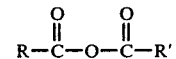

$$R-\overset{O}{\underset{\|}{C}}-O-\overset{O}{\underset{\|}{C}}-R' \qquad I$$

wherein each of R and R' is an alkyl group having 1 to 4 carbons or aryl radical containing electronegative substituents and 6 to about 10 carbons. Straight chain carboxylic acid anhydrides falling within the ambit of formula I include acetic anhydride, propionic anhydride and n-butyric anhydride. Exemplary aryl carboxylic acid anhydrides include p-nitrobenzoic acid anhydride, p-chlorobenzoic acid anhydride, and the like.

These anhydrides can also be cyclic having the formula:

$$\begin{array}{c} \overset{O}{\underset{\|}{C}}-O-\overset{O}{\underset{\|}{C}} \\ \lfloor \underline{\quad Z \quad} \rfloor \end{array} \qquad II$$

wherein Z is an alkylene radical having 2 to 10 carbons, a cycloalkylene radical having 5 to 6 carbons, or o-phenylene. Cyclic carboxylic acid anhydrides falling within the ambit of this formula include succinic anhydride, glutaric anhydride, 1,2-cyclohexanedicarboxylic acid anhydride, phthalic anhydride and substituted homologs thereof.

The criticality of the structure of these anhydrides is demonstrated by the fact that trimethylacetic and benzoic anhydrides do not enhance the rate of peroxide formation. Both trimethylacetic and benzoic anhydrides are known to undergo very slow hydrolysis with relative rates about 0.03 compared to acetic anhydride (1.0) under comparable reaction conditions.

The use of the anhydrides described supra to achieve this effect was unexpected since, a priori, peroxides normally react with anhydrides to form peroxyesters in the presence of acid catalysts and alcohols normally react with anhydrides to form esters in the presence of acid catalysts. However, by choosing suitable anhydrides little or no peroxyester or ester is formed and high yields of the desired di-tertiary peroxides are obtained. Although not wishing to be bound by any theory or explanation of this phenomenon, it is believed that under the reaction conditions specified above the rate of hydrolysis of anhydride to carboxylic acid is more rapid than the reaction between hydroperoxide and anhydride or between alcohol and anhydride.

In general the hydroperoxides used in this invention can be represented by the formula:

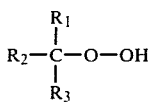

and the tertiary alcohols by the formula:

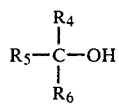

wherein each of $R_1$, $R_2$, $R_3$, $R_4$, $R_5$, and $R_6$ are alkyl having 1 to about 6 carbons, substituted or unsubstituted aryl having 6 to 10 carbons, heteroaryl having 4 to 6 carbons where the heteroatom is oxygen, sulfur or nitrogen, alkyl substituted aryl or heteroaryl as recited above and cyclic substituents formed by combining two of $R_1$, $R_2$, $R_3$, $R_4$, $R_5$, or $R_6$, as for example when $R_1$ and $R_2$ together form an alkylene radical such as, $-(CH_2)_5-$. Where the aryl group is substituted one can use halogen, nitro, acetoxy, ether, alkyl having 1–6 carbons, and like groups.

The preferred tertiary hydroperoxide is cumene hydroperoxide and the preferred tertiary alcohol is cumyl alcohol also known as 2-phenyl-2-propanol. This preferred system affords the preferred reaction product, dicumyl peroxide.

The acid catalyst can be any strong organic or inorganic acid catalyst such as perchloric acid, sulfuric acid, hydrochloric acid, p-toluenesulfonic acid, $-SO_3H$ substituted ion exchange resins, trifluoroacetic acid, and the like acids having $pK_a \leq 2.5$ in aqueous solution at 25° C.

The claimed preparation of di-tertiary peroxide can be effected without added solvent. If desired one can use an inert solvent or mixture of solvents such as, aromatic hydrocarbons, as exemplified by benzene, toluene, cumene, and the like; cycloaliphatic hydrocarbons such as cyclopentane, cyclohexane, cycloheptane, and the like; or carboxylic acids such as acetic acid, propionic acid, and like acids with $pK_a$ values $>2.85$.

Minor amounts of solvents may be present to facilitate handling of reactants as for example, the dilution of perchloric acid catalyst with acetic acid prior to adding the catalyst to the reactants or they may be merely tolerated as a common impurities in the reagent used, as for example, the case of a commercial grade 80% cumene hydroperoxide which contains about 10 to 20% by weight of cumene.

Although the molar ratio of hydroperoxide:alcohol:anhydride can be 1.0:0.2–2.5:0.2–2.0, the preferred ratios are 1.0:0.9–1.5:0.5–1.2. The amount of anhydride may be adjusted to compensate for the instances where water other than that formed during the reaction is present or enters the system.

For the purposes of this invention the amount of strong acid catalyst used is an amount equal to about 0.0001 to 2.0 mole percent of the hydroperoxide used.

This invention is also applicable to the preparation of mixed peroxides as for example, cumyl 1,1-diphenylethyl peroxide, as well as symmetrical peroxides. Bis-peroxides can also be prepared using a bifunctional alcohol, such as, bis-1,4(2-hydroxy-2-propyl)benzene with, for example, cumene hydroperoxide in a 2:1 mole ratio:

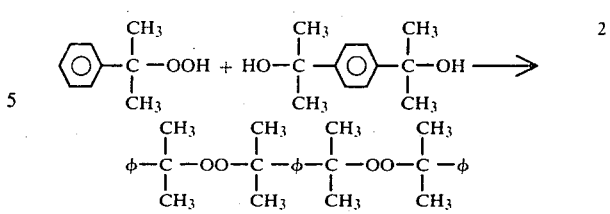

In the alternative a dicumyl hydroperoxide may be interacted with 2-phenyl-2-propanol in a 2:1 mole ratio:

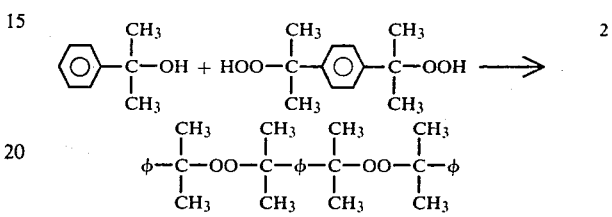

While the reaction temperature may vary between about $-10°$ C. and about $+120°$ C., the preferred temperature range is about 10° to about 80° C.

Pressure is not narrowly critical. Atmospheric pressures as well as superatmospheric and subatmospheric pressures can be used. The preparation of di-tertiary peroxides may be carried out as either as batch and/or a continuous reaction and includes:

(A) a process in which the acid catalyst undiluted or diluted with a solvent is added to a mixture of tertiary hydroperoxide, tertiary alcohol, anhydride, and optionally a solvent;

(B) a process in which a solution of hydroperoxide and anhydride optionally in a solvent is added to a solution of tertiary alcohol and acid catalyst and optionally a solvent;

(C) a process in which the two solutions in the process of (B) are added simultaneously and mixed in a reaction vessel; and (D) where anhydride and hydroperoxide either optionally diluted with solvent are added separately but concurrently to a solution of alcohol, catalyst, and optionally solvent. Variations of these can also be used.

If desired the economics of the claimed method can be improved by recovering the acids formed by anhydride hydrolysis using standard techniques, such as distillation, extraction and the like.

No special equipment is needed to carry out these reactions other than conventional and commercially available reaction vessels, stills, recovery vessels and the like.

The invention is further described in the Examples which follow. All the parts and percentages are by weight unless otherwise specified. All weights of recovered crude reaction products have been corrected to account for analytical samples removed during the reaction.

EXAMPLE 1

THE USE OF ACETIC ANHYDRIDE IN PREPARATION OF DICUMYL PEROXIDE

A mixture consisting of 17.3 grams (92 millimoles) of 81% commercial grade cumene hydroperoxide in cumene, 15.3 grams (109 millimoles) of 2-phenyl-2- propanol (97–100%) and 9.7 grams (95 millimoles) of acetic anhydride was placed in a reaction flask fitted with a thermometer, magnetic stir bar, and a calcium chloride drying tube. The flask was placed in a water bath whose temperature was adjusted by means of copper coil through which cold water was passed and the flask contents was adjusted to 16°±1° C. A solution of 0.75 grams of concentrated perchloric acid (70%) in 100 ml. of glacial acetic acid was prepared, and 4 ml of this solution was added dropwise to the stirred, cooled reaction mixture over a period of 4 minutes. The reaction temperature was maintained at a temperature of 16°±1° C. At appropriate times, a sample of the reaction mixture was removed and quickly quenched with a slight excess of sodium acetate to neutralize the perchloric acid catalyst. A weighed portion of the sample was then analyzed for cumene hydroperoxide by back-titration with sodium thiosulfate after reaction of the hydroperoxide with excess potassium iodide in isopropanol solvent. After a period of 180 minutes reaction time, less than 5% of the hydroperoxide remained unreacted.

After a total of 340 minutes reaction time, the reaction solution was neutralized with excess sodium acetate and dissolved in diethyl ether. The ether solution was washed successively in a separatory funnel with water, a saturated sodium bicarbonate solution and a saturated sodium chloride solution. The ether solution was then dried over anhydrous sodium sulfate, filtered, and the ether was stripped by distillation under vacuum on a rotary evaporator affording a yield of 28.4 grams of crude product. Analysis of the product by gas-liquid chromatography using an internal standard showed it to contain 64% of dicumyl peroxide (73% yield based on the hydroperoxide charged).

CONTROL A—THE EFFECT OF REPLACING ACETIC ANHYDRIDE WITH ACETIC ACID

The procedure in Example 1 was followed charging the flask with 17.3 grams (92 millimoles) of 81% cumene hydroperoxide, 15.2 grams (108 millimoles) of 2-phenyl-2-propanol, 10 grams (167 millimoles) of glacial acetic acid and 4 ml of perchloric acid catalyst solution. The reaction temperature was maintained at 16°±1° C. for 380 minutes by which time only 67% of the hydroperoxide had reacted. The reaction was allowed to warm to about 23° C. in order to complete the reaction. After an additional 970 minutes, 4.9% of the hydroperoxide remained unreacted. The reaction was quenched with excess sodium acetate and worked up as in Example 1 affording 26.3 grams of crude product. Analysis as in Example 1 showed 72% dicumyl peroxide product (76% yield based on hydroperoxide).

The comparison of Example 1 and Control A clearly demonstrates that in the presence of acetic anhydride the desired reaction to produce dicumyl peroxide proceeds at a much faster rate requiring only 180 minutes to achieve about 95% of hydroperoxide consumption whereas the control reaction using acetic acid required at least 1350 minutes and a higher reaction temperature to produce an equivalent amount of the desired product. Thus the anhydride reduced the reaction time by a factor of over 7.5.

EXAMPLE 2

THE USE OF ACETIC ACID SOLVENT

Following the procedure described in Example 1 the reaction flask was charged with 17.3 grams (92 millimoles) of the 81% cumene hydroperoxide, 15.2 grams (108 millimoles) of 2-phenyl-2-propanol, 9.7 grams (95 millimoles) of acetic anhydride and 75 ml glacial acetic acid. The reaction solution was stirred at 18°±1° C. and 4 ml of the perchloric acid catalyst solution in acetic acid was added.

The reaction was maintained at 18°±1° C. and samples were taken and quenched with sodium acetate sulfate as in Example 1. After 36 minutes, 10.3% of the cumene hydroperoxide remained unreacted. After an additional 30 minutes, 7% of the hydroperoxide remained. After another 18 minutes, the reaction was quenched with sodium acetate and the excess acetic acid was removed by rotary evaporation under vacuum at 25°–55° C. The residue was then worked up as in Example 1 affording 25.5 grams of crude product which by analysis was shown to contain 72% of dicumyl peroxide (74% yield based on the hydroperoxide charged).

CONTROL B—REPLACEMENT OF ACETIC ANHYDRIDE BY ACETIC ACID

Using the procedure of Example 2, the reaction flask was charged with 17.3 grams (92 millimoles) of 81% cumene hydroperoxide, 15.2 grams (108 millimoles) of 2-phenyl-2-propanol, and 84 ml of glacial acetic acid. Then 4 ml the perchloric acid catalyst solution described in Example 1 was added dropwise over a period of 5 minutes holding the reaction temperature at 17°±1° C. After 131 minutes, 16.5% of the hydroperoxide remained unreacted and after a total of 245 minutes 8.0% hydroperoxide remained unreacted. The reaction mixture was warmed to 23°±2° C., neutralized with excess sodium acetate, and worked up essentially as in Example 2 to afford 24.6 grams of crude product. Analysis showed the crude product consisted of 77% of dicumyl peroxide (76% yield based on hydroperoxide).

Thus, in this reaction 92% of the hydroperoxide was consumed after 245 minutes reaction time, whereas in the Example 2 in which acetic acid anhydride was present only 66 minutes was required to consume 93% of the hydroperoxide. In each case, the yield of dicumyl peroxide was essentially the same.

In the presence of the anhydride the reaction time in acetic acid solvent decreased by about a factor of 3.7.

A comparison of Examples 1 and 2 or Controls A and B demonstrates that the reaction time is reduced when the reaction is run in acetic acid solvent, whether or not anhydride is present. This appears to be merely an ordinary solvent effect. Regardless of the explanation, the fact is that reduced reaction time is observed when the anhydride is used.

EXAMPLE 3

USE OF CUMENE SOLVENT

Using the procedure described in Example 1, the flask was charged with 46.5 grams (93 millimoles) of commercial grade cumene hydroperoxide (30.3% in cumene), 15.2 grams (108 millimoles) 2-phenyl-2-propanol (97+% purity), 9.7 grams (95 millimoles) of acetic anhydride and 45 ml (38.8 grams, 320 millimoles) of cumene and the reaction mixture cooled to 17°±1° C. Four ml of the perchloric acid catalyst solution described in Example 1 was added dropwise and samples of the reaction mixture removed periodically for analysis. After 247 minutes 9.4% of the hydroperoxide remained unreacted and after 307 minutes 6.7% remained unreacted. The reaction was warmed to room temperature and reaction was allowed to proceed for additional 45 minutes, after which the reaction mixture was quenched with sodium acetate. The reaction mixture was washed with water and sodium bicarbonate solution and then sodium chloride solution as in Example 1 and dried over anhydrous sodium sulfate.

The solvent was removed from the filtered solution on a rotary evaporator under vacuum at 50°–95° C. to afford 28.3 grams of crude product. Analysis of the crude product showed that it contained 68% dicumyl peroxide (76% yield based on hydroperoxide).

CONTROL C—THE EFFECT OF OMITTING ANHYDRIDE

Using the procedure of Example 3, the reaction flask was charged with 46.5 grams (93 millimoles) of 30.3% cumene hydroperoxide in cumene, 15.2 grams (108 millimoles) of 2-phenyl-2-propanol, and 55 ml (47.4 grams, 390 millimoles) of cumene. Then 4 ml of the perchloric acid catalyst solution described in Example 1 was added at a reaction temperature of about 17° C. After 254 minutes, 76% of the hydroperoxide remained unreacted. The temperature was allowed to rise to room temperature (23° C.) and after an additional 21 hours 66% of the hydroperoxide remained. Droplets of water had formed on the wall of the vessel. After another 3 days the remaining hydroperoxide was 61%.

This Control clearly shows that even at higher temperatures and much longer reaction times, the reaction of cumyl hydroperoxide with 2-phenyl-2-propanol does not proceed as readily as in Example 3 wherein acetic anhydride was present.

CONTROL D—REPLACEMENT OF ACETIC ANHYDRIDE BY ACETIC ACID

Following the procedure described in Example 3, the flask was charged with 46.5 grams (93 millimoles) of 30.3 cumene hydroperoxide in cumene, 15.3 grams (109 millimoles) of 2-phenyl-2-propanol, 45 ml (38.8 grams, 320 millimoles) of cumene and 10 grams (167 millimoles) of glacial acetic acid. Then 4 ml of the perchloric acid catalyst solution described in Example 1 was added dropwise at a reaction temperature of 17°±1° C. After 4 hours, 60% of the hydroperoxide remained unreacted. The reaction was warmed to room temperature and after an additional 17 hours 38% of the hydroperoxide remained unreacted. The reaction was then forced to completion by adding more catalyst solution and heating the reaction to 40° C. for approximately 32 hours and then at room temperature for an additional 66 hours. Workup of the reaction mixture as in Example 3 afforded 30.8 grams crude product. Analysis showed the crude product to contain 66% dicumyl peroxide (81% yield based on hydroperoxide).

This control illustrates that a small solvent effect obtains by adding acetic acid to the cumene solvent which increases the reaction rate somewhat from that in Control C. However, the reaction still proceeds very much slower than the reaction of Example 3 where acetic anhydride was used.

EXAMPLES 4–12 and CONTROL E

Using the procedure described in Example 1 the following Examples were run with certain modifications indicated hereinafter.

A solution (A) of the reactant alcohol and perchloric acid catalyst solution (and optionally solvent) was placed in the reaction flask which, as in Example 1, was placed in a bath to control the reaction temperature. Alternatively, a jacketed reaction flask with temperature-regulated water circulating through the jacket was used. A second solution (B) of hydroperoxide and (optionally) organic anhydride and/or solvent was added dropwise to the stirred solution (A) over a specific time (about 30 minutes) while maintaining the reaction temperature at the selected temperature. After the addition was complete, samples were taken, quenched with sodium acetate and analyzed for hydroperoxide by titration as in the previous Examples. When the reaction was complete the catalyst was neutralized with sodium acetate and the reaction solution was worked up as in Example 1, Example 2 or Example 3. The experimental quantities of the reactants are shown in Table 1. The results of the variables incorporated into these Examples are delineated in the Table 2.

TABLE I

| | Solution A | | | | Solution B | | | | |
|---|---|---|---|---|---|---|---|---|---|
| | Alcohol[a] | | HClO₄[b] | Solvent[c] | CHP[d] | | Anhydride[e] | | Solvent[c] |
| Example | gm | millimoles | ml | gm | gm | millimole | gm | millimole | gm |
| 4 | 16.4 | 117 | 4.0 | | 18.6 | 100 | 10.7 | 105 | |
| 5 | 16.4 | 117 | 4.0 | | 18.6 | 100 | | | |
| 6 | 16.4 | 117 | 4.0 | | 18.6 | 100 | | | 12.6A |
| 7 | 16.4 | 117 | 4.0 | | 18.6 | 100 | 5.1 | 50 | |
| 8 | 16.4 | 117 | 4.0 | | 18.6 | 100 | 10.7 | 105 | |
| 9 | 16.4 | 117 | 4.0 | | 18.6 | 100 | | | 12.6A |
| 10 | 16.4 | 117 | 4.0 | | 18.6 | 100 | 14.1[f] | 108 | |
| 11 | 15.2 | 108 | 4.0 | 55.0A | 17.3 | 92 | 9.7 | 95 | 20.A |
| 12 | 15.2 | 108 | 4.0 | 55.0A | 17.3 | 92 | | | 30.A |
| Control E | 16.4 | 117 | 4.0 | | 18.6 | 100 | 24.2[g] | 105 | |

[a]2-phenyl-2-propanol (≧97% purity);
[b]Prepared from 7.0 gm 70% perchloric acid diluted to 1000 ml with glacial acetic acid except Examples 15 and 16 used a solution prepared with 0.75 gm HClO₄ in 100 ml acetic acid;
[c]A = glacial acetic acid;
[d]Cumene hydroperoxide (81–82% in cumene);
[e]Acetic anhydride except in Examples 10 and Control E;
[f]Propionic anhydride;
[g]Benzoic anhydride.

TABLE 2

| Example | Addition[a] Time, min. | Temp. (±1° C.) | CHP[b] Unreacted, % | At Total[c] Time (min.) | Yield[d] DCP, % |
|---|---|---|---|---|---|
| 4 | 29 | 40 | 2.5 | 35 | 82 |

TABLE 2-continued

| Example | Addition[a] Time, min. | Temp. (±1° C.) | CHP[b] Unreacted, % | At Total[c] Time (min.) | Yield[d] DCP, % |
|---|---|---|---|---|---|
| 5 | 30 | 40 | 9.4 (32.3) (43.7) | 1475(257)(95) | 87 |
| 6 | 30 | 40 | 7.2 | 275 | 94 |
| 7 | 30 | 40 | 7.8 | 160 | 84 |
| 8 | 31 | 30 | 3.7 | 60 | 90 |
| 9 | 32 | 30 | 5.0 (34.1) | 1088 (120) | 91 |
| 10 | 30 | 30 | 3.8 | 176 | 80 |
| 11 | 48 | 28 | 1.8 | 48 | 88 |
| 12 | 33 | 28 | 23.3 | 48 | 89 |
| Control E | 30 | 40 | 65.3 | 160 | — |

[a]Time over which solution B added to solution A.
[b]CHP = cumene hydroperoxide (numbers in parehtheses give additional data with the corresponding time in column 5).
[c]Total reaction time beginning with the addition of solution B to A.
[d]DCP = dicumyl peroxide, by analysis as in Example 1.

Example 4 shows the results of using the acetic anhydride at a reaction temperature of 40° C.

Example 5 clearly shows that with no anhydride or solvent, the reaction is much slower than in Example 4 (by a factor of over 40).

Example 6 shows that in comparison with Example 4, where an acetic anhydride was used, its replacement by acetic acid solvent slows the reaction by factor of over 7.

Example 7 shows that with about half of the proportion of acetic anhydride of Example 4, the reaction still proceeds faster than either the procedure of Example 5, (a factor of improvement of about 9) or Example 6, (a factor improvement of about 1.5).

Example 8 shows the results when the reaction of Example 4 is run at a lower temperature, viz., 30° C.

Example 9 shows the results when the reaction of Example 6 is run at a lower temperature, viz., 30° C. Thus, in the comparison of Example 8 and Example 9 the reaction rate is improved in Example 8 compared to Example 9 by a factor of over 18, which is even greater than the factor of about 7 seen in the comparison between Examples 4 and 6 which were run at the higher temperature, viz., 40° C.

Example 10 shows that using propionic anhydride in place of acetic anhydride (Example 8) results in somewhat longer reaction time compared to Example 8, but also results in a large reduction in reaction time compared to Example 9 wherein no anhydride was used. The effect of propionic anhydride (Example 10), compared to that of acetic anhydride (Example 8) is consistent with the slower relative hydrolysis rate of propionic anhydride (0.52) compared to acetic anhydride (1.0) as reported by A.R. Butler et al., J. Chem. Soc., 976 (1962).

Example 11 illustrates the reaction similar to Example 8 carried out in acetic acid solvent.

Example 12 shows the effect of omitting the acetic anhydride used in the Example 11. As in previous comparisons, although acetic acid solvent results in a small promotion of the reaction (See for instance the comparison of Examples 11 and 8), a large increase in reaction rate (i.e., a reduction in overall reaction time) is observed when an organic anhydride is present as shown by the fact 23.3% of the hydroperoxide remains after 48 minutes in Example 12 compared to only 1.8% hydroperoxide in Example 11.

Control E shows that the use of benzoic anhydride does not result in an increase in reaction rate. Thus, after 160 minutes reaction time only 35% of the cumene hydroperoxide was consumed whereas in Example 5 with no anhydride present about 56% of the hydroperoxide had been consumed after 95 minutes. The lack of a rate enhancement with benzoic anhydride, which is in contrast to the effect of acetic anhydride (Example 4), is consistent with the reported relative rate of hydrolysis of benzoic anhydride in dioxane-water solution (relative rate 0.03 compared 1.0 for acetic anhydride, C. A. Bunton, N. A. Fuller, S. G. Perry, and V. J. Shiner, J. Chem. Soc., 2918 [1963]).

EXAMPLE 13

THE USE OF CIS-1,2-CYCLOHEXANEDICARBOXYLIC ANHYDRIDE

The reaction described in Example 2 was repeated with 14.7 gm (95 millimoles) cis-1,2-cyclohexanedicarboxylic anhydride substituted for the acetic anhydride. After a total reaction time of 125 minutes (at 18°±1° C.), 9.9% of the cumene hydroperoxide remained unreacted. The reaction was quenched (sodium acetate) after a total time of 245 minutes and, after recovery in a manner similar to Example 2, afforded 35.9 gm crude product which contained about 70% dicumyl peroxide. (An approximate value for dicumyl peroxide was obtained in this case because the elution of cis-1,2-cyclohexanedicarboxylic acid on the gas-liquid chromatography column partially overlapped with the dicumyl peroxide).

In this reaction about 90% of the hydroperoxide had reacted after 125 minutes, whereas in Control B 245 minutes was required to achieve 92% hydroperoxide conversion.

EXAMPLE 14

THE USE OF SUCCINIC ANHYDRIDE

The reaction described in Example 2 was repeated with 9.5 gm (95 millimoles) succinic anhydride substituted for the acetic anhydride. The succinic anhydride was not completely soluble in the reaction medium. After a total reaction time of 95 minutes (at 18°±1° C.), 15.9% of the cumene hydroperoxide remained unreacted; after a total time of 155 minutes, 9.0% of the cumene hydroperoxide remained unreacted. The reaction was quenched (sodium acetate) after a total time of 261 minutes and, after recovery in a manner similar to Example 2, afforded 27.7 gm crude product which contained 80.7% dicumyl peroxide (89% yield based on hydroperoxide).

In this reaction about 84% of the hydroperoxide was consumed after 95 minutes compared to about 83.5% hydroperoxide consumed after 131 minutes in Control B. Thus, the reaction rate was enhanced in the presence of the anhydride even though the anhydride was only partially soluble.

EXAMPLE 15
THE USE OF PHTHALIC ANHYDRIDE

The reaction described in Example 2 was repeated with 14.1 gm (95 millimoles) phthalic anhydride substituted for the acetic anhydride. The phthalic anhydride was not completely soluble in the reaction medium. After a total reaction time of 95 minutes (at 18°±1° C.), 15.1% of the cumene hydroperoxide remained unreacted; after a total reaction time of 155 minutes, 7.9% of the hydroperoxide remained unreacted. The reaction was quenched (sodium acetate) after a total reaction time of 333 minutes and, after recovery in a manner similar to Example 2, afforded 28.8 gm crude product which contained 77.7% dicumyl peroxide (82% yield based on hydroperoxide).

In spite of the incomplete solubility of the phthalic anhydride in the reaction medium, about 85% of the cumene hydroperoxide was consumed after 95 minutes, whereas in Control B 131 minutes was required to consume about 83.5% of the hydroperoxide.

In the previous Examples (13–15) the use of succinic, phthalic, and 1,2-cyclohexanedicarboxylic anhydride resulted in an increased reaction rate compared to Control B in a manner similar to that observed with acetic anhydride (Example 2). This is consistent with hydrolysis rates of these anhydrides in water or organic-water solutions which rates are reported to be similar to or somewhat faster than the comparable hydrolysis rate of acetic anhydride (C. A. Bunton, N. A. Fuller, S. G. Perry, and V. J. Shiner, J. Chem. Soc., 2918 [1963]; L. Eberson and L. Landstrom, Acta. Chem. Scand. 26, 239 [1972]).

CONTROL F
THE USE OF TRIMETHYLACETIC ANHYDRIDE

The reaction in Example 2 was repeated with 17.7 gm (95 millimoles) trimethylacetic anhydride substituted for the acetic anhydride. After a total reaction time of 185 minutes (at 18°±1° C.), 17.2% of the cumene hydroperoxide remained unreacted; and after a total reaction time of 327 minutes, 8.2% hydroperoxide remained unreacted. The reaction was quenched (sodium acetate) after a total reaction time of 429 minutes and, after recovery in a manner similar to Example 2, afforded 37.6 gm crude reaction produce which contained 57.6% dicumyl peroxide (80% yield based on hydroperoxide).

In this example, in contrast to the previous examples with various anhydrides, the reaction rate is not enhanced by the presence of anhydride. Thus, in Control B 92% of the cumene hydroperoxide was consumed after 245 minutes but in the present reaction with trimethylacetic anhydride 327 minutes was required to consume about 92% of the hydroperoxide.

The lack of reaction rate enhancement in this example, in contrast to the effect of acetic anhydride in Example 2, is consistent with reported slow rate of hydrolysis of trimethylacetic anhydride (relative rate 0.03 compared to 1.0 for acetic anhydride at 25° C., A. R. Butler and V. Gold, J. Chem. Soc., 976 [1962]).

CONTROL G—THE EFFECT OF CHLOROACETIC ANHYDRIDE

A three-necked flask fitted with a thermometer, magnetic stir bar, and drying tube was charged with 8.97 gm chloroacetic anhydride and 7.2 gm dioxane solvent. Cumene hydroperoxide (9.3 gms, 81% in cumene) was added dropwise at an initial temperature of 27.6° C. over a period of 15 minutes. At the end of the addition the reaction temperature was 30.5° C. After an additional 14 minutes the reaction temperature had reached 38° C. and the temperature continued to rise to 70.5° C. after another 19 minutes. The reaction temperature then began to decrease to room temperature.

The behavior of this system in which an exothermic reaction was observed to occur between cumene hydroperoxide and chloroacetic anhydride (in contrast to the behavior when cumene hydroperoxide is mixed with reagent acetic anhydride which results in no observable exotherm) indicates the well known catalyzed decomposition of cumene hydroperoxide (phenol and acetone are products of this decomposition). Chloroacetic acid produced by reaction between cumene hydroperoxide and chloroacetic anhydride decomposes the cumene hydroperoxide and, therefor, this anhydride is not a suitable replacement for acetic anhydride to enhance the reaction between cumene hydroperoxide and 2-phenyl-2-propanol to form dicumyl peroxide.

It is known that the reaction between acetic acid and cumene hydroperoxide is very slow (W. E. Cass and A. K. Bahl, J. Org. Chem., 39, 3602 [1974]). The contrast between acetic anhydride and chloroacetic anhydride is consistent with the relative acidity of the corresponding acids, i.e., chloroacetic acid is a stronger acid ($pK_a = 2.82$ in water at 25° C.) compared to acetic acid ($pK_a = 4.75$).

Although the invention has been described in its preferred forms with a certain degree of particularity, it is understood that the present disclosure has been made only by the way of example and that numerous changes can be made without departing from the spirit and scope of the invention.

What is claimed is:

1. In the method for the preparation of di-tertiary peroxides by the interaction of a tertiary aryl or alkyl hydroperoxide with a tertiary aryl or alkyl alcohol in the presence of a strong acid catalyst, the improvement which comprises carrying out said interaction in the presence of at least one readily hydrolyzable anhydride of carboxylic acids having a $pK_a > 2.85$ in a molar ratio of hydroperoxide:alcohol:anhydride of about 1.0:0.2–2.5:0.2–2.0 at a temperature of about −10° C. to about 120° C., said anhydride having a formula selected from the group consisting of

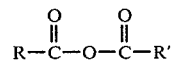

wherein each of R and R' is selected from the group consisting of alkyl groups having 1 to 4 carbons or aryls containing at least one electronegative substituent and 6 to 10 carbons, and

wherein Z is a divalent radical selected from the group consisting of alkylene radicals having 2 to 10 carbons, cycloalkylene radicals having 5 to 6 carbons or o-phenylene.

2. Method claimed in claim 1 wherein the anhydride has the formula:

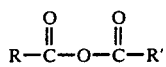

3. Method claimed in claim 1 wherein the anhydride has the formula

4. Method claimed in claim 2 wherein the anhydride is acetic anhydride.

5. Method claimed in claim 2 wherein the anhydride is propionic anhydride.

6. Method claimed in claim 3 wherein the anhydride is succinic anhydride.

7. Method claimed in claim 1 wherein the molar ratio of hydroperoxide:alcohol:anhydride is about 1:0.9–1.5:0.5–1.2.

8. Method claimed in claim 1 wherein the temperature is about 10°–80° C.

9. Method claimed in claim 1 wherein the hydroperoxide is cumene hydroperoxide and the alcohol is 2-phenyl-2-propanol.

10. Method claimed in claim 4 wherein the hydroperoxide is cumene hydroperoxide and the alcohol is 2-phenyl-2-propanol.

11. Method claimed in claim 1 wherein the carboxylic acid or acids produced by in situ hydrolysis are recovered as a by-product or by-products.

12. Method claimed in claim 4 wherein the acetic acid produced by in situ hydrolysis is recovered as a by-product.